Figure 1:
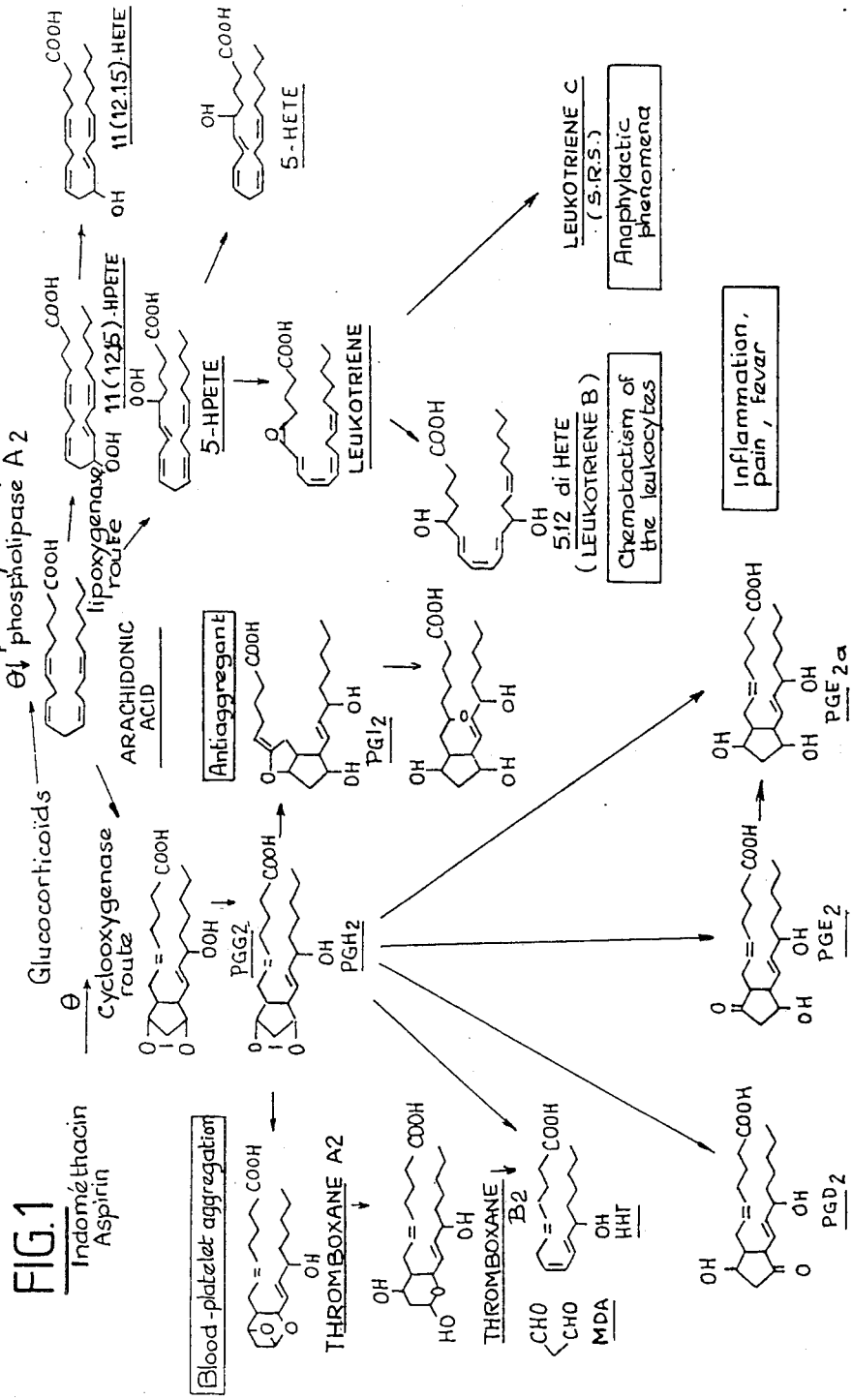

United States Patent [19]

Coquelet et al.

[11] Patent Number: 4,656,184
[45] Date of Patent: Apr. 7, 1987

[54] 2-(N-SUBSTITUTED HYDRAZONE), THIAZOLES USEFUL AS ANTI-INFLAMMATORIES

[76] Inventors: Claude Coquelet, 113 Rue des Lilas, 34980 Saint Gely du Fesc; Chantal Bertez, Rue des Etats du Languedoc Résidence "Le Languedoc" Batiment A4, 34000 Montpellier; Claude Bonne, 12 bis Avenue Aristide Briand, 94360 Bry-sur-Marne; Daniel Sincholles, 343 Avenue de la Trémoulette, 34980 Saint-Clement, all of France

[21] Appl. No.: 589,114
[22] PCT Filed: Jun. 17, 1983
[86] PCT No.: PCT/FR83/00126
§ 371 Date: Feb. 7, 1984
§ 102(e) Date: Feb. 7, 1984
[87] PCT Pub. No.: WO84/00007
PCT Pub. Date: Jan. 5, 1984

[30] Foreign Application Priority Data

Jun. 18, 1982 [FR] France ............................ 82 10687

[51] Int. Cl.$^4$ .................. A61K 31/425; C07D 277/50
[52] U.S. Cl. .................................. 514/370; 548/193; 548/194; 548/195; 548/198
[58] Field of Search ............... 548/190, 193, 194, 198, 548/195; 514/370

[56] References Cited

U.S. PATENT DOCUMENTS 3,786,094  1/1974  Perronnet et al. .................. 544/398

OTHER PUBLICATIONS

Schilt et al., Talanta, vol. 27, pp. 55–58, (1980).
Beyer et al., Berichte, vol. 89, No. 5, pp. 1095–1099, (1956).
Yamada et al., Chemical Abstracts, vol. 73:78537g, (1970).

Primary Examiner—Robert Gerstl
Assistant Examiner—Stephen M. Kapner
Attorney, Agent, or Firm—Young and Thompson

[57] ABSTRACT

This invention relates to therapeutic compositions comprising, as active ingredient, N-substituted hydrazones having the formula:

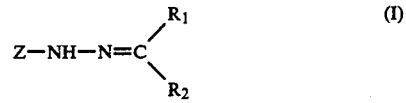

(I)

in which Z is a 2-thienyl or phenyl radical.

Said compositions have an anti-inflammatory activity, particularly in the ocular field.

7 Claims, 7 Drawing Figures

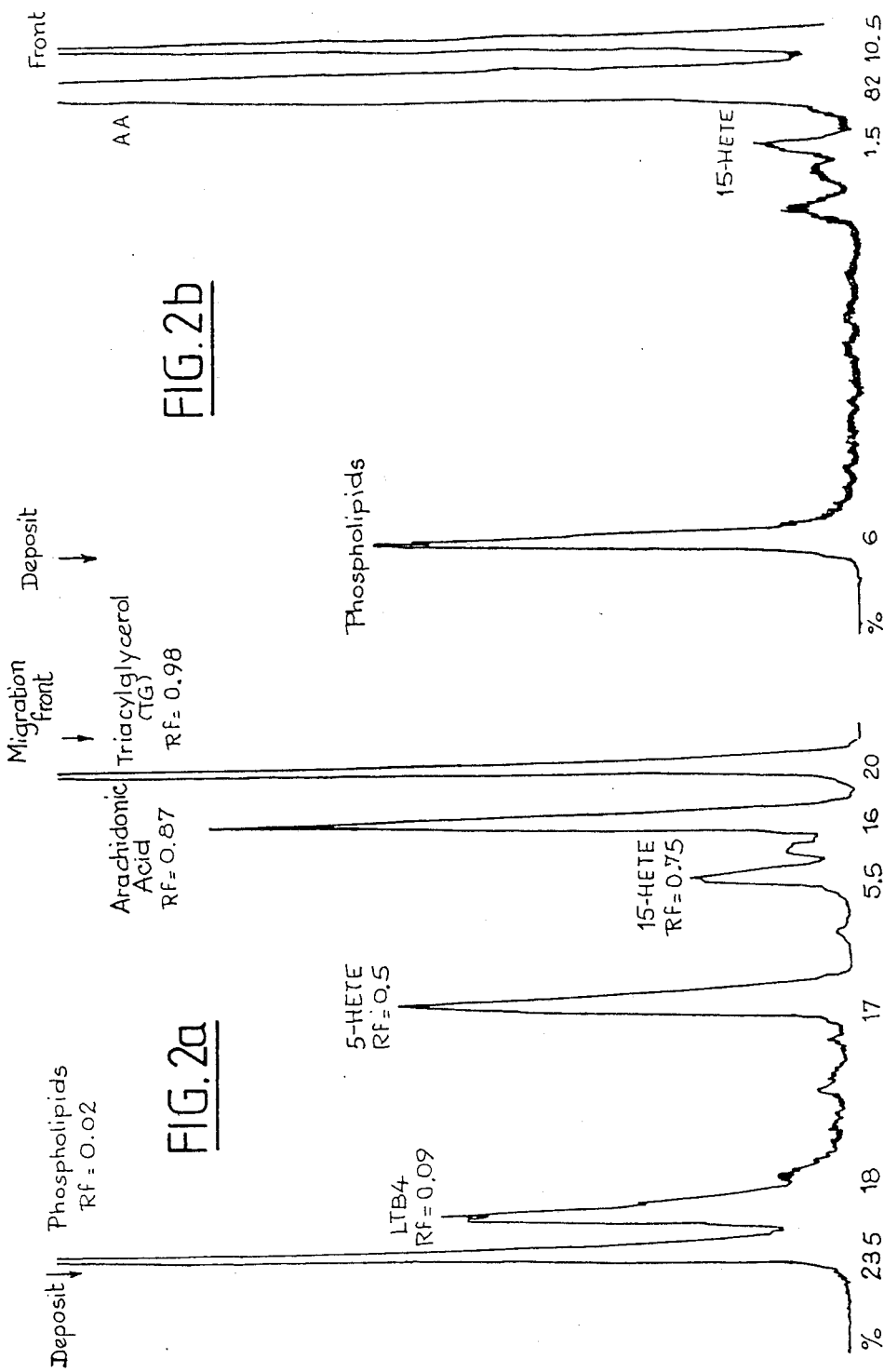

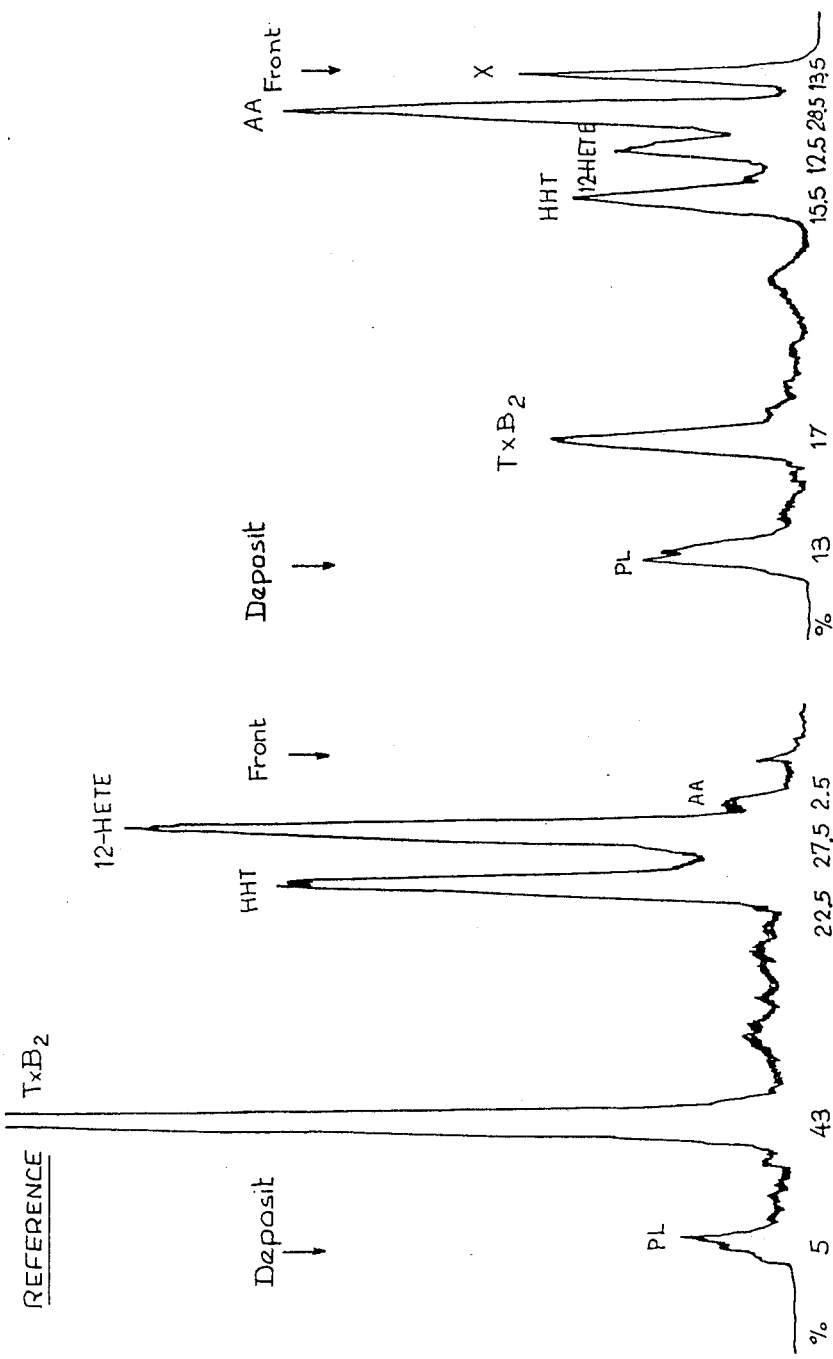

2-(N-SUBSTITUTED HYDRAZONE), THIAZOLES USEFUL AS ANTI-INFLAMMATORIES

This invention relates to new therapeutic compositions containing N-substituted hydrazones as active ingredient. Said compositions are useful in the treatment of inflammatory phenomena and, in particular, in the treatment of ocular inflammatory phenomena.

The ocular inflammatory response is the sequence of events induced by a lesion or irritation of the tissues of the eye. It is reflected by an increase of the intraocular pressure, a leukocytic infiltration in the tissues and the liquids of the eye, an increase of the protein level in the aqueous humor and an uveitis.

Although the nature of the inflammatory response may be extremely varied, and it may have a multiplicity of mediators (kinines, histamine, etc.), there is always production of proinflammatory metabolites of arachidonic acid at the level of the injured tissue, i.e., prostaglandines ($PG_s$) and hydroxy-eicosatetraenoic acids ($HETE_s$). This production is increased by the infiltration of the polymorphonuclear leukocytes ($PMN_s$) towards the site of the inflammation, which, in turn, produce $PG_s$ and $HETE_s$ in the course of the phagocytosis. The known biologic effects of the $HETE_s$ are, inter alia, chemokinetism and chemotactism with respect to the $PMN_s$.

The $PG_s$ and $HETE_s$ are metabolites of arachidonic acid, a $C_{20}$ fatty acid. They are synthetically produced according to two distinct routes, which are diagrammatically represented in FIG. 1:

the cyclooxygenase route leads successively to endoperoxides $PGG_2$ and $PGH_2$, precursors of various $PG_s$ of Series 2. Among them, $PGE_2$ and $PGI_2$ (prostacycline) possess in particular a vasodilator action.

the lipoxygenase route leads to un-cyclized mono- and -dihydroxyeicosatetraenoic acids ($HETE_s$) most of which are proinflammatory acids, just as their precursors, the corresponding hydroxyperoxy acids ($HPETE_s$) Thus, 5,12-diHETE or leucotriene $B_4$ ($LTB_4$) is the most potent chemotactic agent known in the case of human leukocytes. Additionally, metabolites of this route are involved in allergic phenomena such as asthma.

In contrast to the $PG_s$ which have common precursors, $PGG_2$ and $PGH_2$, the lipoxygenase products have different precursors:

12-HPETE, in the blood-platelets, synthetically formed under the action of a 12-lipoxygenase, leads to the formation of 12-HETE.

in the leukocytes, 5-HPETE and 15-HPETE are predominantly involved leading to 5-HETE, 5,12-diHETE and 15-HETE.

Research for therapeutic agents liable to oppose the inflammatory reaction was oriented towards the following routes:

inhibition of the release of arachidonic acid by the glucocorticoids. The major drawback of the glucocorticoids is to induce an increase of the intraocular pressure and to favor the formation of a glaucoma or a cataract.

inhibition of the cyclooxygenase route by nonsteroid anti-inflammatory agents (such as Aspirin, Indomethacin, Tanderil). Recent experimental investigations, however, show that Indomethacin increases leukocytic infiltration in the aqueous humor by inhibiting the cyclooxygenase route, it favors the lipoxygenase route and, thus, the release of chemotactic products.

The simultaneous inhibition of the 5-lipoxygenase and of the cyclooxygenase route is liable to block the synthesis of the different pro-inflammatory mediators in the same manner as the glucocorticoids, but without exhibiting the detrimental effects thereof.

The present invention is precisely based on the discovery that certain hydrazones inhibit both the leukocytic lipoxygenase and the formation of blood-platelet prostanoids. Thus, they oppose the development of the vascular phase of inflammation (involving the $HETE_s$).

Therefore, the present invention relates to therapeutic compositions which contain, as active ingredient, a compound of the formula:

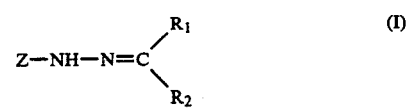

(I)

in which:

Z represents a 2-thiazolyl or phenyl group;

$R_1$ represents a hydrogen atom, a $C_{1-6}$alkyl group, a $C_{5-7}$cycloalkyl group, a hydroxy group, a $C_{1-6}$alkoxy group, a carboxy group, a carboxy($C_{1-6}$alkyl) group, a 1-imidazolyl ($C_{1-10}$alkyl) group, a group of the formula —$NHR_3$ in which $R_3$ is a hydrogen atom, a $C_{1-6}$alkyl group, a $C_{5-7}$cycloalkyl group, an amino($C_{1-6}$alkyl) group, or a 5–7 membered nitrogen-containing non-aromatic heterocyclic group which may contain another heteroatom selected from nitrogen and oxygen, or a group of the formula

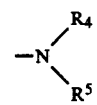

in which, together with the nitrogen atom to which they are attached, $R_4$ and $R_5$ form a 5–7 membered non-aromatic heterocycle which may contain another heteroatom selected from nitrogen and oxygen and which may be substituted with a $C_{1-6}$alkyl group, $R_2$ represents a carboxy($C_{1-6}$alkyl) group, a ($C_{1-6}$ alkoxy)carbonyl($C_{1-6}$alkyl) group, an aryl group having 6–16 carbon atoms or a heteroaromatic group comprising one or two heteroatoms selected from nitrogen, oxygen and sulfur and having 3–15 carbon atoms, the aryl and heteroaromatic groups may be substituted with one or more hydroxy, amino, carboxy or carboxy($C_{1-6}$alkyl) groups, or $R_1$ and $R_2$, together with the carbon atom to which they are attached, form a radical selected from the bi- or polycyclic aromatic hydrocarbon radicals having 8–16 carbon atoms, the non-aromatic mono- or polycyclic hydrocarbon radicals having 5–16 carbon atoms and the bi- or polycyclic heteroaromatic radicals comprising one or two heteroatoms selected from nitrogen, oxygen and sulfur and having 6–15 carbon atoms, which radicals may be substituted with a carboxy group;

or a pharmaceutically acceptable acid addition salt thereof.

In the above definition, by the term "pharmaceutically acceptable acid addition salts" are meant the salts which possess the biological properties of the free bases, without having an undesirable effect. Such salts may typically be those formed with inorganic acids such as hydrochloric acid, hydrobromic acid, sulfuric acid, nitric acid, phosphoric acid, acidic metal salts such as disodium orthophosphate and monopotassium sulfate, and organic acids such as formic acid, acetic acid, propionic acid, glycolic acid, oxalic acid, fumaric acid, citric acid, malic acid, methanesulfonic acid, lactic acid, succinic acid, tartaric acid and pamoic acid.

The term "halogen" denotes chlorine, bromine or iodine.

By the term "bi- or polycyclic aromatic hydrocarbon radicals" are meant bi- or polycyclic radicals having at least one aromatic cycle. Examples of such radicals include the 1,2,3,4-tetrahydro-naphthylidene and indanylidene radicals.

By the term "non-aromatic mono- or polycyclic hydrocarbon radicals" are meant cyclic hydrocarbon radicals which do not include an aromatic cycle. The cyclohexylidene radical is an example of such radicals.

By the term "bi- or polycyclic heteroaromatic radicals" are meant bi- or polycyclic radicals having at least one aromatic cycle. Examples of such radicals include the chromanylidene, chromenylidene, phenylchromanydene and indolinylidene radicals.

Examples of non-aromatic nitrogen containing heterocyclic groups within the definition of $R_3$ include the pyrrolidinyl, imidazolinyl, pyrazolidinyl, piperidyl, piperazinyl or morpholino groups.

Examples of non-aromatic heterocyclic groups within the definition of $-NR_4R_5$ include the 1-pyrrolidinyl, piperidino, 1-piperazinyl or morpholino groups.

Examples of heteroaromatic groups within the definition of $R_2$ include the thienyl, furyl, pyrrolyl, pyridyl, imidazolyl and isoxazolyl groups.

A preferred class of compounds of the formula (I) is that in which:
Z represents a 2-thiazolyl group,
$R_1$ represents a methyl group, and
$R_2$ represents a $(C_{1-6}alkoxy)carbonyl(C_{1-6}alkyl)$ group, a thienyl group or a phenyl group substituted with one or more hydroxy groups; or
$R_1$ and $R_2$, together with the carbon atom to which they are attached, form a chromanydene, an indanylidene or a 1,2,3,4-tetrahydro-naphthylidene group.

Another preferred class of compounds of the formula (I) is that in which:
Z represents a phenyl group,
$R_1$ represents a group of the formula $-NHR$ or $-NR_4R_5$, typically an amino group or a methylpiperazinyl group, and
$R_2$ represents an aryl or heteroaromatic group, typically a phenyl group.

A number of compounds of the formula (I) are known compounds (see Chemische Berichte, Vol. 85, n° 12, 1123–1127; Chemische Berichte, Vol. 89, n° 5, 1095–1099;; Talanta, Vol. 27, 55–58; Bull. Soc.Chim., 1973, 9–10, 2843).

This invention relates also to new compounds of the formula (1), i.e., compounds having the formula

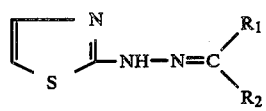

(I)

in which:

$R_1$ represents a hydrogen atom, a $C_{1-6}alkyl$ group, a $C_{5-7}cycloalkyl$ group, a hydroxy group, a $C_{1-6}alkoxy$ group, a halogen atom, an amino group or a $(C_{1-6}alkyl)amino$ group, $R_2$ represents a carboxy($C_{1-6}alkyl$) group, a $(C_{1-6}alkoxy)carbonyl(C_{1-6}alkyl$ group), a thienyl group, a furyl group, a 1-imidazolyl($C_{1-10}alkyl$) group, a phenyl group substituted with one or more hydroxy groups, or $R_1$ and $R_2$, together with the carbon atom to which they are attached, form a radical selected from the bi- or polycyclic aromatic hydrocarbon radicals having 8–16 carbon atoms, the non-aromatic mono- or polycyclic hydrocarbon radicals having 5–16 carbon atoms and the bi- or polycyclic heteroaromatic radicals comprising one or two heteroatoms selected from nitrogen, oxygen and sulfur and having 6–15 carbon atoms, and their pharmaceutically acceptable acid addition salts.

The new compounds and the known compounds may be obtained by conventional methods.

Thus, the compounds of the formula (I) in which $R_1$ is a hydrogen atom, an alkyl or cycloalkyl group, may be prepared by reaction of a hydrazine of the formula $$Z-NH-NH_2 \quad (II)$$

with a ketone of the formula

(III)

in which $R_1$ and $R_2$ are as defined above.

The reaction may be effected typically in alcohol solution, in the presence of a catalytic amount of an acid such as acetic acid or hydrochloric acid. The reaction is generally effected at elevated temperature, advantageously at the reflux temperature of the solvent, using equimolar amounts of hydrazine (II) and ketone (III), and for a period of time of from 15 mn to 3 hrs.

In the case of ketones (III) having a carboxy group, the reaction may be effected by refluxing equimolar amounts of hydrazine (II) and ketone (III) within a 10% aqueous acetic acid solution, for 1–3 hrs.

Hydrazine (II) may also be reacted with ketone (III) by adding to ketone (III), dissolved in an alcohol, an equimolar amount of 2-thiazolyl-hydrazine hydrochloride in aqueous solution. The reaction occurs at room temperature and may be obtained, for example, by stirring for 15 mn.

The hydrazones of the formula (I) in which $R_1$ represents a hydroxy group, may be prepared by reacting hydrazine (II) in pyridine solution with an equimolar amount of acid chloride of the formula

(IV)

The reaction may be effected at 5° C., with stirring.

The compounds of the formula (I) in which $R_1$ is an alkoxy group may be obtained from compounds of the formula (I) in which $R_1$ is a hydroxy group, according to conventional etherification methods.

The compounds of the formula (I) in which $R_1$ is a $-NHR_3$ or $-NR_4R_5$ group may be obtained from a hydrazonic acid chloride of the formula

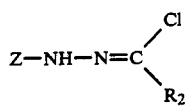

by addition of an amine —NHR$_3$ or —NHR$_4$R$_5$.

The compounds of the formula (I) in which Z is a 2-thiazolyl group may also be prepared by reaction of a ketone (III) with thiosemicarbazide and reaction of the resulting thiosemicarbazone with 1,2-dichloro-2-ethoxyethane, chloroacetaldehyde, chloroacetaldehyde diethylacetal, or 1,2-dichloro-ethyl acetate, according to the following sequence:

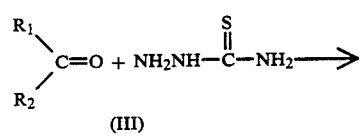

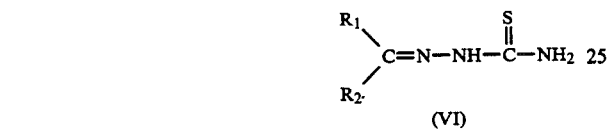

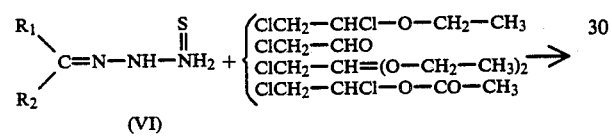

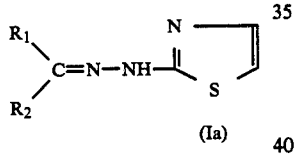

The reaction of thiosemicarbazone (VI) with, for example, chloro acetaldehyde diethylacetal may be effected by heating to reflux, for one hour, an alcohol solution of equimolar amounts of the reactants.

The pharmaceutically acceptable acid addition salts may be prepared in a conventional manner by reaction of the free bases with an acid or a salt, typically dissolved in an alcohol.

In the following Tables Ia and Ib are given examples of compounds used in the present invention. Said compounds were prepared according to the following procedures:

Procedure A

Equimolar amounts of ketone (III) and hydrazine (II) in a methanol solution containing 5% acetic acid are heated to boiling for 15 minutes, under a nitrogen stream.

After which 2 volumes of water are added, the mixture is triturated, the resulting precipitate is suction filtered and the crude product is recrystallized.

Procedure B

To a pyridine solution of hydrazine (II) cooled to 5° C. is added an equimolar amount of acid chloride (IV). The mixture is stirred at 5° C. for 15 minutes and is then left aside at room temperature for 48 hours. The resulting material is concentrated to half volume in vacuo, after which it is poured into water and the precipitate formed is suction filtered. After washing with water, the product is recrystallized from methanol.

Procedure C

A methanol solution of hydrazone (I) is saturated in the cold with a stream of gaseous HCl. Five volumes of ether are added thereto, after which the precipitate thus formed is suction filtered and recrystallized.

Procedure D

Equimolar amounts of hydrazone (I) and acid are refluxed for 5 minutes in methanol; after which the material is cooled, ether (1 volume) is added thereto, the resulting crude salt is suction filtered and is then recrystallized.

Procedure E

Ammonia is bubbled at 0° C. for 3 hours in a tetrahydrofuran solution of 0.2 mole hydrazonic acid chloride of the formula (V). After filtering the ammonium chloride thus formed, the solvent is evaporated in vacuo at room temperature. An ether solution of the crude base is saturated with a stream of gaseous hydrochloric acid. After which the hydrochloride is suction filtered, and is then recrystallized.

Procedure F

To a benzene solution of 0.2 mole hydrazonic acid chloride of the formula (V) is added a benzene solution of 1 mole amine, at 5° C., over 30 minutes. Stirring is continued a further 3 hours at 20° C., after which the amine hydrochloride is filtered off. The procedure is then identical with the procedure described above.

Proceure G

Identical with procedure F, except that the addition is effected over 15 minutes at room temperature, after which stirring is maintained for 1 hour at room temperature and, finally, one hour under reflux conditions.

Table Ia gives examples of compounds of the formula

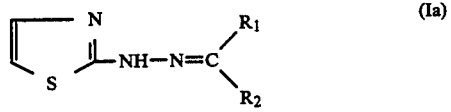

and Table Ib gives examples of compounds of the formula

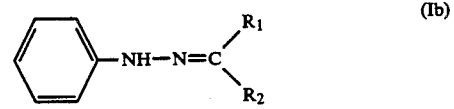

TABLE Ia

COMPOUNDS OF THE FORMULA Ia

| Example | =C(R₁)(R₂), salt 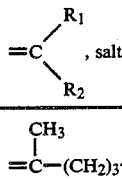 | R | M.P. (°C.) recryst. solvent | Appearance of the crystals | Yield, weight % | Procedure |
|---|---|---|---|---|---|---|
| 1 | =C(CH₃)−(CH₂)₃−CO₂C₂H₅ | | 90−2 MeOH* | Golden Yellow | 56 | A |
| 1a | =C(CH₃)−(CH₂)₃−CO₂C₂H₅, HCl | | 89−91 EtOH* | Colorless | 51 | C |
| 2 | =C(CH₃)−(CH₂)₃−CO₂H | | 183−5 MeOH | light brown | 54 | A |
| 3 | 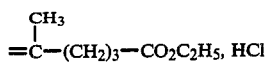 | | 160−2 MeOH | Light beige | 60 | A |
| 3a | 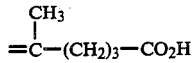, HCl | | 194−6 MeOH | Yellow | 56 | C |
| 3b | 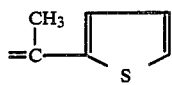, COOH COOH | | 174−6 MeOH | Light beige | 57 | D |
| 3c | 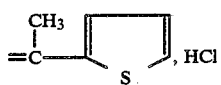 | H, COOH / HOOC, H | 194−6 MeOH | Light beige | 53 | D |
| 3d | | 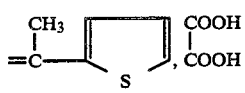 | 152−4 MeOH | Light beige | 53 | D |
| 3e | | 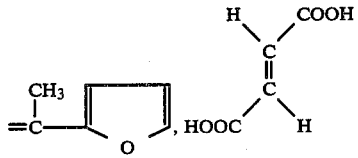 | 150−2 MeOH | Light beige | 36 | D |
| 4 | | 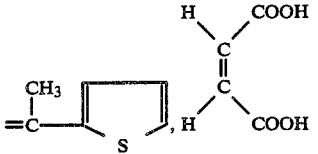, HCl | 126−8 MeOH + Et₂O* | Parma violet | 10 | C |
| 5 | | 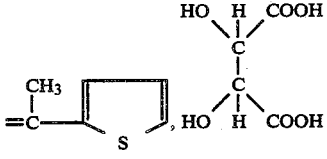 | 204−6 DMF* | Straw yellow | 56 | A |
| 5a | | 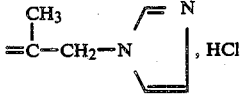, HCl | 189−91 MeOH + Et₂O | Colorless | 86 | C |

TABLE Ia-continued
COMPOUNDS OF THE FORMULA Ia $=C\begin{smallmatrix}R_1\\R_2\end{smallmatrix}$, salt

| Example | R | M.P. (°C.) recryst. solvent | Appearance of the crystals | Yield, weight % | Procedure |
|---|---|---|---|---|---|
| 6 | 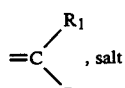 | 176–8 MeOH | Colorless | 30 | A |
| 6a | 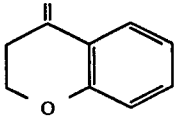 | 226° (dec.) MeOH | Colorless | 65 | C |
| 7 | 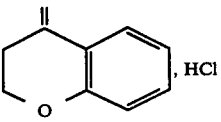 | 169–71 MeOH | Light beige | 30 | A |
| 7a | 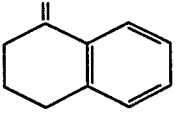 | 219–21 MeOH | Colorless | 72 | C |
| 8 | 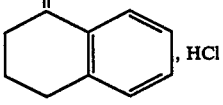 | 176–8 MeOH | Light beige | 40 | A |
| 8a | 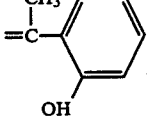 | 208–10 MeOH | Light beige | 41 | C |
| 9 | 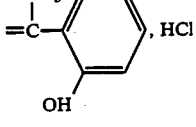 | 177–9 MeOH | Colorless | 30 | A |
| 9a | 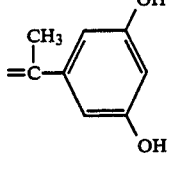 | 233–5 MeOH | Light beige | 50 | C |
| 10 | 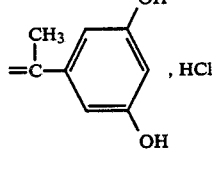 | 125–7 MeOH | Light beige | 20 | A |
| 10a | 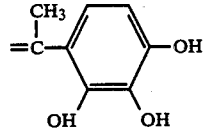 | 240 (dec.) | Light beige | 50 | C |

TABLE Ia-continued
COMPOUNDS OF THE FORMULA Ia
| Example | =C(R₁)(R₂), salt | R | M.P. (°C.) recryst. solvent | Appearance of the crystals | Yield, weight % | Procedure |
|---|---|---|---|---|---|---|
| 11 | | 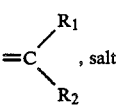 | 213–5 MeOH | Brick yellow | 20 | B |
| 11a | | 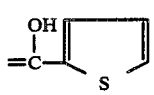 | 195–7 MeOH + Et₂O | Light beige | 53 | C |
| 12 | | 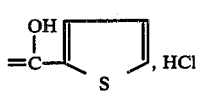 | 93–5 MeOH | Colorless | 30 | A |
| 12a | | 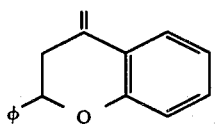 | 119–21 MeOH + Et₂O | Colorless | 50 | C |
| 13 | | 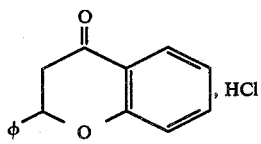 | 177–9 MeOH | Colorless | 57 | A |
| 13a | | 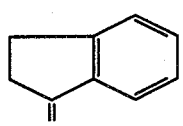 | 239–41 MeOH | Straw yellow | 71 | C |
| 14 | 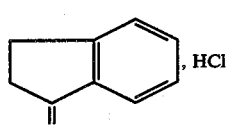 | | >250 MeOH | Straw yellow | 40 | A |
| 15 | 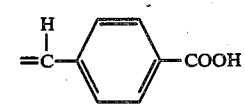 | | 241–3 MeOH | Light beige | 70 | A + C |
| 16 | 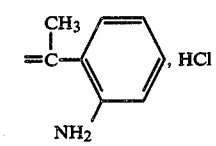 | | 204–6 MeOH | Golden Yellow | 54 | A |
| 17 | 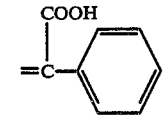 | | 232–4 MeOH | Orange | 53 | A |
| 18 | 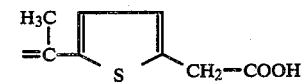 | | 184–6 MeOH | Straw yellow | 45 | A |

TABLE Ia-continued
COMPOUNDS OF THE FORMULA Ia $=C\begin{matrix}R_1\\R_2\end{matrix}$, salt

| Example | R | M.P. (°C.) recryst. solvent | Appearance of the crystals | Yield, weight % | Procedure |
|---|---|---|---|---|---|
| 19 | (CH₂—CH₂—N-pyrimidine group on thiophene) | 216-8 MeOH | Straw yellow | 15 | A |
| 20 | (chromene-2-carboxylic acid) HOOC | 186-8 MeOH | Colorless | 57 | A |

*MeOH = methanol
EtOH = ethanol 95°
*Et₂O = diethyl ether
DMF = dimethylformamide

TABLE Ib
COMPOUNDS OF THE FORMULA (Ib)

$=C\begin{matrix}R_1\\R_2\end{matrix}$, salt

| Example | R₂ | M.P. (°C.) Recryst. solvent | Appearance of the crystals | Yields, weight % | Procedure |
|---|---|---|---|---|---|
| 21 | phenyl-NH₂, HCl | 190-2 EtOH + Et₂O | Colorless | 60 | E |
| 22 | phenyl-CH-N-morpholine, HCl | 227-9 EtOH | Straw yellow | 40 | F |
| 23 | phenyl-CH-N-piperazine-CH₃, HCl | 222-4 EtOH = Et₂O | Colorless | 54 | F |
| 24 | phenyl-CH-NH-N-piperidine, HCl | 212-4 EtOH | Light beige | 60 | F |
| 25 | phenyl-CH-NH-N-morpholine, HCl | 114-6 EtOH + Et₂O | Colorless | 26 | G |

Results of pharmacological and toxicological investigations which demonstrate the properties of the compounds of the formula (I) are given below.

1. "IN VITRO" BIOCHEMICAL PHARMACOLOGY 1.1. Inhibition of the 5-lipoxygenase of the peritoneal leukocytes of rabbits (PMN$_s$)

Methods

. Preparation of a suspension of rabbit PMN$_s$

The peritoneal leukocytes of rabbits are obtained and prepared according to the technique described by P. Borgeat and B. Samuelson (J. Biol. Chem. 254, n° 8, p. 2643, 1979).

. Metabolism of $^{14}$C-Arachidonate

The incubation and extraction methods are those described by J. Y. Vanderhoek & co-workers (J. Biol. Chem. 55, 21, 10064, 1980).

Results

FIG. 2a shows a chromatographic profile characteristic of the metabolism of $^{14}$C-AA in the peritoneal PMN$_s$ of rabbits compared with the one obtained in the presence of the compound of Example 3b (50 µM)(FIG. 2b). The latter (FIG. 2b) provides evidence of the inhibition of the metabolism of the 5-lipoxygenase route.

The percent inhibition of the 5-lipoxygenase is determined as a function of the concentration of each compound. The concentration of product that inhibits the metabolism by a factor of 50% (IC$_{50}$) is inferred from those curves.

Many compounds of the formula (I) inhibit by a factor of 50% the formation of 5-HETE and LTB$_4$ at a concentration from 2 µM and 20 µM.

A number of results are given in Table II for illustrative purposes.

TABLE II

| Example | IC$_{50}$ (× 10$^{-6}$ M) in the PMNS | | | IC$_{50}$ (× 10$^{-6}$ M) in the blood platelets | | |
|---|---|---|---|---|---|---|
| | LTB$_4$ | 5 HETE | 15 HETE | T × B$_2$ | HHT | 12 HETE |
| 1 | <2 | <2 | >50 | >50 | >50 | >50 |
| 1a | 13 | <2 | n.d. | 12 | 50 | n.i. |
| 3 | 7 | 18 | n.i. | 50 | 20 | 3 |
| 3a | 18 | 15 | 40 | 13 | 21 | 30 |
| 3b | 13 | 10 | 40 | 10 | >50 | 10 |
| 3c | 2 | 10 | >50 | 10 | >50 | 14 |
| 3d | 2 | <2 | n.i. | 10 | 50 | 22 |
| 3e | <2 | <2 | n.d. | n.d. | n.d. | n.d. |
| 4 | n.i. | n.i. | 2 | >50 | >50 | >50 |
| 7 | 8 | 6 | 2 | 10 | 16 | 40 |
| 7a | 6 | 5 | 2 | 5 | 15 | n.i. |
| 15 | <25 | <25 | n.d. | <25 | 25 | n.i. |
| 20 | n.i. | n.i. | n.d. | 15 | 20 | n.i. |
| 21 | 10 | 20 | n.d. | 10 | 10 | n.i. |
| 23 | 25 | 25 | n.d. | 25 | 25 | 25 | n.i. = no inhibition
n.d. = not determined

1.2. Inhibition of the metabolism of $^{14}$C-Arachidonate in the blood platelets of rabbits Methods . Preparation of a platelet-rich plasma (PRP)

A 12 ml blood sample is taken, by the intracardiac route, on ACD (anticoagulant consisting of an aqueous solution containing 0.27 g citric acid, 0.5 g disodium citrate and 0.02 g glucose per 20 ml water), at a rate of 1 volume ACD per 6 volumes blood. The blood is centrifuged at 200 g for 10 minutes and the supernatant (PRP) is collected. It is again centrifuged at 1500 g for 15 minutes. The blood-platelet sediment is washed with Buffer I (NaCl: 8 g/l, Tris: 1.21 g/l, KCl: 0.2 g/l, Gelatin: 2.5 g/l; the material is heated at 90° C. to dissolve the gelatin, after which are added glucose: 1 g/l, and N,N'-ethyleneglycol bis(β-aminoethyl ether,)tetraacetic acid or EGTA: 0.075 g/l). The suspension is centrifuged at 1500 g for 10 minutes, and the sediment is taken up into Buffer II (NaCl: 8 g/l, Tris: 1.21 g/l, KCl: 0.2 g/l, CaCl$_2$: 0.145 g/l, MgCl$_2$0.2 g/l, gelatin: 2.5 g/l; this material is heated to 90° C., after which glucose (1 g/l) is added, and the pH is adjusted to a value of 7.4 with 0.1 N HCl), . Metabolism of $^{14}$C-Arachidonate The blood-platelet suspension (0.4 ml/tube) is preincubated at 37° C. for 15 minutes, either with 10 µl DMSO (reference), or with varying concentrations of products to be treated dissolved in 10 µl DMSO.

The incubation is effected in the presence of $^{14}$C-Arachidonate (1 µg, 0.2 µCi) distributed within 0.1 ml Buffer II. It is blocked after 15 minutes by means of 50 µl citric acid and 250 µl saturated NaCl.

Results

The chromatographic profile characteristic of the metabolism of $^{14}$C-Arachidonate in the blood platelets of rabbits is modified in the presence of cyclooxygenase inhibitors.

Figure 3B:
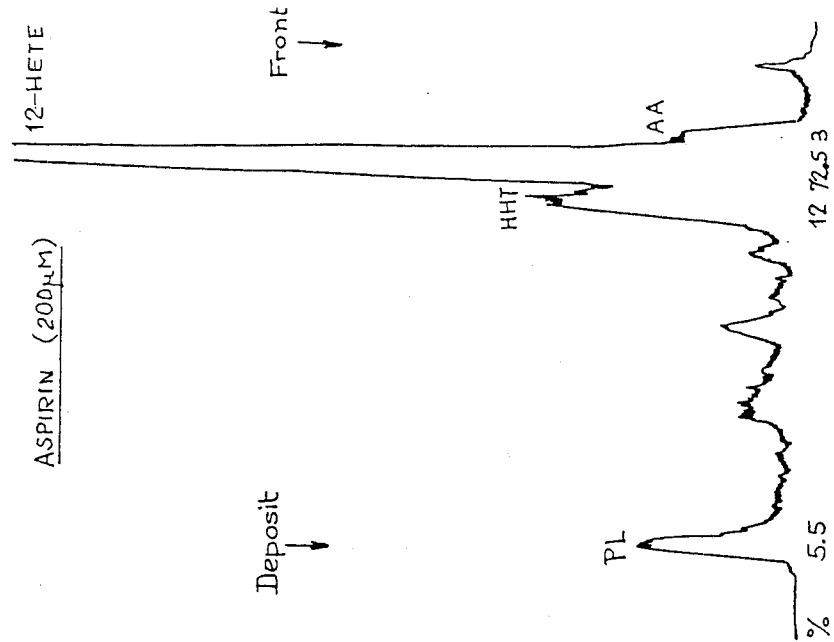
Figure 3A:
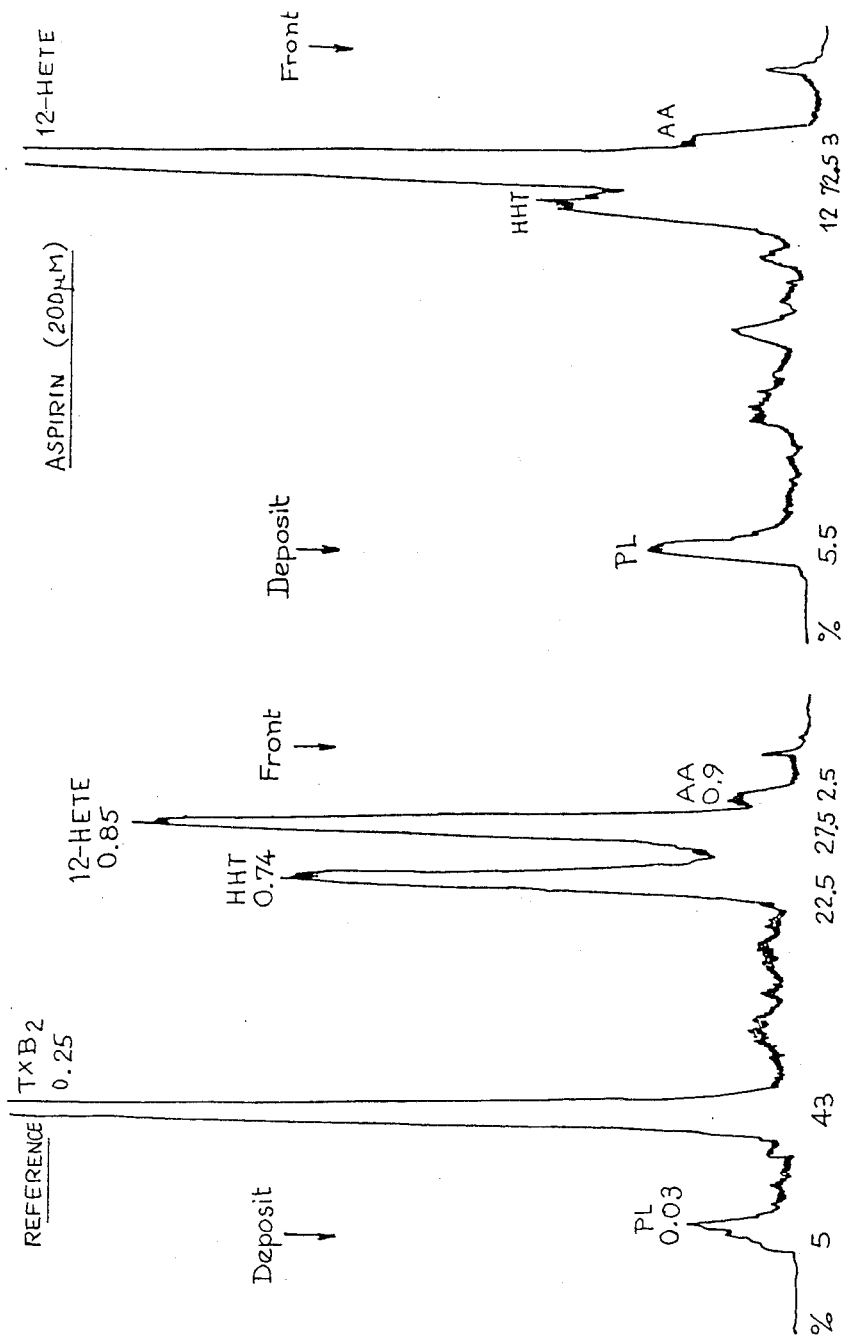

FIGS. 3A and 4a give the chromatographic profile of the metabolism of $^{14}$C-AA in the blood-platelets of rabbits compared with that obtained in the presence of Aspirin (FIG. 3b) and of the compound of Example 3b (FIG. 4b).

The percent inhibition of the prostanoids and the 12lipoxygenase routes is evaluated by the determination of the disappearance of 12-HETE and of thromboxane B$_2$ (TxB$_2$) as a function of varying concentrations of each compound.

This test provides evidence that the compounds of the formula (I) which exhibit a good activity on the 5-lipoxygenase route are generally the more active on TxB$_2$.

Specific results are given in Table II for illustrative purposes.

It is also apparent from FIG. 3b that, in contrast, Aspirin does not inhibit the 12-lipoxygenase route.

2. FUNCTIONAL PHARMACOLOGY

Cutaneous anti-inflammatory activity determined by the inhibition of the edema of the ear in rats following topic administration.

This activity is determined by means of the method according to G. Tonelli and co-workers (Endocrinology, 1965, 77, 625–634).

The effect of various concentrations of each compound is determined in at least seven rats.

Inflammation is inhibited by a factor of 50% at the following concentrations:

| | | |
|---|---|---|
| Dexamethasone | 1 mg/ml | (2.5 µmoles/ml) |
| Indomethacin | no inhibition | |
| Aspirin | 70 mg/ml | (233 µmoles/ml) |
| NDGA⊕ | 12.5 mg/ml | (41 µmoles/ml) |

| Compound of Ex. 3b | 16 mg/ml | (57 μmoles/ml) |

⊕Nordihydroguaiaretic acid

3. ACUTE TOXICITY

The test animals used are Swiss mice (NMRI-Han). The average weight of the male animals is 30 g, that of the females is 25 g.

The acute toxicity investigation was conducted by the intraperitoneal route.

The compounds, dissolved in DMSO, are injected under the ventral side of the peritoneum, at increasing dosages.

The reference group is administered DMSO under the same conditions (2.5 ml.kg$^{-1}$).

The LD$_{50}$ is determined after an observation period of 14 days.

Results

Following Table III gives the values of the 50% lethal dosages together with the 5% confidence interval.

A slight difference between sexes is noted.

TABLE III

Parenteral LD$_{50}$ of the compound of Example 3b in mice (mg · kg$^{-1}$)

| Male mice | Female mice |
|---|---|
| 105 ± 24 | 155 ± 32 |

The therapeutic compositions of this invention may be administered to humans or animals by the topical, oral or parenteral (including intra-articular) route.

They may be formulated as solid, semi-solid or liquid preparations. Examples include tablets, capsules, suppositories, injectable solutions or suspensions, ointments, oily or aqueous collyria, mouth-wash preparations, nasal and otological solutions, and also the sustained-action formulations.

In such compositions, the active ingredient is generally in admixture with one or more of the usual pharmaceutically acceptable excipients familiar to the man skilled in the art.

The topically administrable therapeutic compositions may contain typically from 0.5% to 5% by weight active ingredient.

The orally or parenterally administrable therapeutic compositions may typically contain from 1% to 60% by weight active ingredient.

The amount of active ingredient administered is obviously dependent on the patient to be treated, on the route of administration and on the severity of the disease. For oral or parenteral administration, however, the daily dosage regimen may be from 0.25 to 5 mg/kg/day, i.e., in a human having a body weight of 70 kg, a dosage of 17.5 to 350 mg/kg/day, and preferably of 25-250 mg/day.

In view of their anti-oxydant properties, the compounds of the formula (I) and their pharmaceutically acceptable acid addition salts are also useful as preservatives and anti-oxydants in the human and animal food industry.

We claim:

1. A compound selected from the group consisting of compounds of the formula:

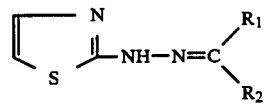

in which:

R$_1$ is selected from hydrogen, C$_{1-6}$alkyl, C$_{5-7}$cycloalkyl, hydroxy, C$_{1-6}$alkoxy, amino, (C$_{1-6}$amino, carboxy and carboxy C$_{1-6}$alkyl, R$_2$ is selected from thienyl, furyl, 1-imidazolyl-(C$_{1-10}$alkyl), and carboxy (C$_{1-6}$alkyl) thienyl, and pharmaceutically acceptable acid addition salts thereof.

2. A compound as claimed in claim 1, wherein R$_1$ is selected from hydrogen, C$_{1-6}$alkyl, hydroxy, carboxy and carboxy C$_{1-6}$alkyl and R$_2$ is thienyl, or a pharmaceutically acceptable acid addition salt thereof.

3. A compound as claimed in claim 1, wherein R$_1$ is C$_{1-6}$alkyl and R$_2$ is thienyl, or a pharmaceutically acceptable acid addition salt thereof.

4. A compound of the formula:

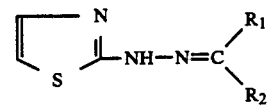

in which:

R$_1$ is methyl and R$_2$ is thienyl, or a pharmaceutically acceptable acid addition salt thereof.

5. A therapeutic composition having a simultaneous inhibition activity on lypoxygenase and cycloxyoxygenase containing an effective amount of a compound as claimed in claim 1, said amount being effective simultaneously to inhibit sand cycloxygenase and said lypoxygenase.

6. A therapeutic composition having an anti-inflammatory activity containing an effective amount of a compound as claimed in claim 1, said amount being effective to inhibit inflammation.

7. Process for the treatment of inflammatory phenomena, which comprises administering to a human in need thereof an effective amount of a compund as claimed in claim 1, said amount being effective to inhibit said inflammatory phenomena.

* * * * *